United States Patent [19]
Alert et al.

[11] Patent Number: 5,728,373
[45] Date of Patent: Mar. 17, 1998

[54] COSMETIC AND DERMATOLOGICAL SUNSCREEN COMPOSITIONS CONTAINING THIOLS AND/OR THIOL DERIVATES

[75] Inventors: Dirk Alert, Hamburg; Heinrich Gers-Barlag, Kummerfeld, both of Germany; Leon T. Van Den Broeke, Leiden; Gerard M. J. Beijersbergen van Henegouwen, Koudekerk, both of Netherlands

[73] Assignees: Beiersdorf AG, Hamburg, Germany; Rijksuniversiteit Leiden, Leiden, Netherlands

[21] Appl. No.: 670,295

[22] PCT Filed: Aug. 17, 1993

[86] PCT No.: PCT/EP93/02188

§ 371 Date: Feb. 27, 1995

§ 102(e) Date: Feb. 27, 1995

[87] PCT Pub. No.: WO94/04129

PCT Pub. Date: Mar. 3, 1994

Related U.S. Application Data

[63] Continuation of Ser. No. 381,847, Feb. 27, 1995, abandoned.

[30] Foreign Application Priority Data

Aug. 26, 1992 [DE] Germany .......................... 42 28 455.4

[51] Int. Cl.$^6$ .................. A61K 7/42; A61K 7/00
[52] U.S. Cl. .................. 424/59; 424/401; 424/70.51
[58] Field of Search .................. 424/59, 401, 70.51, 424/70.9

[56] References Cited

U.S. PATENT DOCUMENTS

| | | | |
|---|---|---|---|
| 4,827,016 | 5/1989 | Morgan | 560/16 |
| 4,992,267 | 2/1991 | DenBeste et al. | 424/71 |
| 5,208,014 | 5/1993 | Dubief et al. | 424/71 |

*Primary Examiner*—Sally Gardner-Lane
*Attorney, Agent, or Firm*—Sprung Kramer Schaefer & Briscoe

[57] ABSTRACT

Cosmetic and dermatological light protection formulations, characterized by an active content of thiols and/or thiol derivatives.

8 Claims, No Drawings

COSMETIC AND DERMATOLOGICAL SUNSCREEN COMPOSITIONS CONTAINING THIOLS AND/OR THIOL DERIVATES

This application is a continuation of application Ser. No. 08/381,847, filed on Feb. 27, 1995 which is abandoned, which claims a filing date of Aug. 17, 1993 under 35 U.S.C. 371.

BACKGROUND OF THE INVENTION

The present invention relates to light protection agents, in particular cosmetic and dermatological light protection agents.

The damaging effect of the ultraviolet component of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity.

The narrower range around 308 nm is stated as having the maximum erythema activity of sunlight.

Numerous compounds are known for protection against UVB radiation, these being derivatives of 3-benzylidenecamphor, of 4-aminobenzoic acid, of cinnamic acid, of salicylic acid, of benzophenone and also of 2-phenylbenzimidazole.

It is also important to have filter substances available for the range between about 320 nm and about 400 nm, the so-called UVA range, since its rays can also cause damage. Thus, it has been proved that UVA radiation causes damage to the elastic and collagenic fibres of connective tissue, which ages the skin prematurely, and that it is to be regarded as the cause of numerous phototoxic and photoallergic reactions. The harmful influence of UVB radiation can be intensified by UVA radiation.

DESCRIPTION OF THE PRIOR ART

Certain derivatives of dibenzoylmethane are therefore used for protection against rays in the UVA range, although the photostability of these derivatives (Int. J. Cosm. Science 10, 53 (1988)) is not adequate.

However, UV radiation can also lead to photo-chemical reactions, the photochemical reaction products then intervening in skin metabolism.

Such photochemical reaction products are chiefly free radical compounds, for example hydroxyl radicals. Undefined free radical photoproducts which are formed in the skin itself can also display uncontrolled secondary reactions because of their high reactivity. Singlet oxygen, an excited state of the oxygen molecule without free radicals, however, can also occur under UV irradiation, as can short-lived epoxides and many other compounds. Singlet oxygen is distinguished, for example, by an increased reactivity compared with the triplet oxygen usually present (free radical ground state). Nevertheless, excited, reactive (free radical) triplet states of the oxygen molecule also exist.

In order to prevent these reactions, antioxidants and/or agents which trap free radicals can additionally be incorporated into the cosmetic or dermatological formulations.

The compounds, some of which are mentioned above, which are employed as light protection agents for cosmetic and dermatological light protection formulations are distinguished by a good light protection action. However, they have the disadvantage that to date it has been difficult to incorporate them into such formulations in a satisfactory manner. Furthermore, these compounds are pure UV-absorbing agents and are unsuitable as agents which trap free radicals.

It has already been proposed to employ vitamin E, a substance having a known antioxidative action, in light protection formulations, but here also, the action achieved remains far below that hoped for.

SUMMARY OF THE INVENTION

However, it was surprising and not to be foreseen by the expert that cosmetic and dermatological light protection formulations having an active content of thiols and/or thiol derivatives remedy the disadvantages of the prior art.

It was not to be foreseen that the thiols or thiol derivatives according to the invention or the cosmetic or dermatological formulations according to the invention would provide better protection against damage by UV radiation act better as an antioxidant act better as an agent which traps free radicals prevent bonding of harmful photoproducts to lipids, DNA and proteins to a better extent than the formulations of the prior art. Furthermore, it was not to be foreseen that the thiols or thiol derivatives according to the invention or the cosmetic or dermatological formulations according to the invention would have a sufficiently high stability for use lead to products tolerated by the skin not intervene in the skin's own microorganism flora counteract light-induced aging of the skin.

In particular, it was not to be predicted that the thiols or thiol derivatives according to the invention or the cosmetic or dermatological formulations according to the invention would be distinguished by a pronounced delayed action ("retarded action"). If particular emphasis is to be placed on this retarded action, the thio esters and thio ethers are particularly preferred.

The thiols or thiol derivatives according to the invention or the cosmetic or dermatological formulations according to the invention furthermore are particularly suitable for penetration into deeper-lying layers of skin, where they can display their action in an advantageous manner.

The thiols or thiol derivatives according to the invention or the cosmetic or dermatological formulations according to the invention furthermore astonishingly are suitable for controlled prophylaxis and/or treatment of UV-induced skin damage.

If the thiols or thiol derivatives according to the invention or the cosmetic or dermatological formulations according to the invention are to be used for protection or prophylaxis against UV-induced hair damage, the thiols or thiol derivatives which are unsubstituted on the thiol group or the cosmetic or dermatological formulations according to the invention are preferred.

Formulations which comprise N-acetylcysteine and act as tanning agents were indeed known from EP-A 219 455. In particular, this publication refers to the fact that N-acetylcysteine promotes pigment formation and is employed chiefly for this purpose. A certain additional antierythematous action, which is claimed in the publication mentioned, is said to make it suitable for cosmetic formulations. However, this publication does not report the advantageous properties of the present invention, that is to say the advantages described above.

EP-A 138 262 describes a combination of panthenol, carrageenin and compounds chosen from the group consisting of methionine, cysteine, N-acetyl-cysteine and S-acetylcysteine, and furthermore other constituents. This combination is used for the treatment of eczema and dyshidrosis caused by sunlight. This publication also gives no teaching which could point in the direction of the present invention.

Thiols in the context of the present invention are to be understood as organic compounds which are characterized by the —SH group. Thiol derivatives in the context of the present invention are organic compounds which are either derivatives which retain the —SH group or are thio ethers or thio esters, in which case the —SH group is converted into the —SR group.

Compounds which are to be understood as being identical to the thiols or thiol derivatives according to the invention in the context of the present invention are those which are formed by tautomerism, di- or oligomerization by hydrogen bonding, hydration or other spontaneous rearrangement from the thiols or thiol derivatives according to the invention. If a derivative is in equilibrium with an isomer by a different type of rearrangement, for example migration of an alkyl group, this isomer is regarded as being included in the thiols and thiol derivatives according to the invention.

If several mesomeric or tautomeric forms of the thiols according to the invention are conceivable, only one mesomeric or tautomeric form is given for the characterization, as is customary in chemistry.

Preferred thiols are

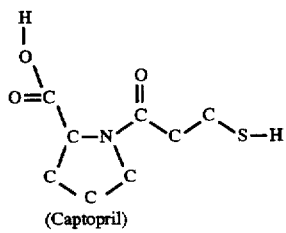
(Captopril)

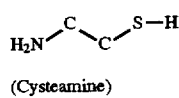
(Cysteamine)

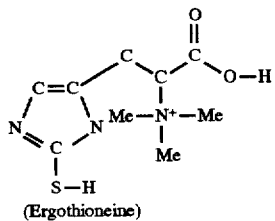
(Ergothioneine)

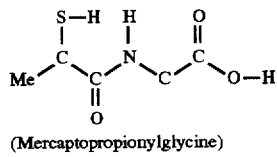
(Mercaptopropionylglycine)

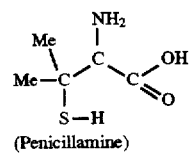
(Penicillamine)

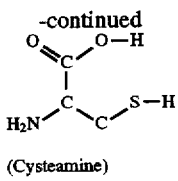
(Cysteamine)

The hydrogen atoms on the carbon atoms are usually omitted in this description for simplicity. To avoid confusion, this simplification is usually deviated from in the case of derivatives, and groupings are characterized more precisely where it seems appropriate: for example Me (=methyl) or Et (=ethyl).

DESCRIPTION OF THE PREFERRED EMBODIMENTS

Particularly preferred derivatives in the cosmetics according to the invention are derived from the parent substance cysteine as follows:

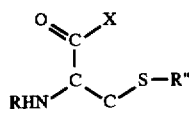

The radical X can be chosen from the group consisting of —O—R' and —NRR'. The radicals R, R' and R" independently of one another are: H, $C_{1-18}$-alkyl or -alkenyl or $C_{1-18}$-acyl.

It is preferable here to choose the organic radicals such that the organic radicals R, R' and R" independently of one another are: H, ethyl or acetyl. X furthermore can also advantageously symbolize the —NH$_2$ group.

However, it is also advantageous, where appropriate, to choose the thiol derivatives according to the invention from the following group:

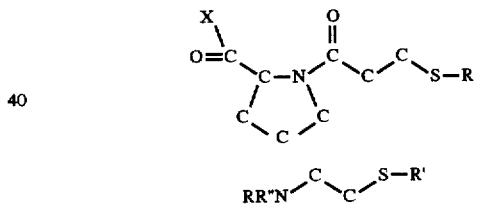

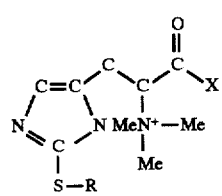

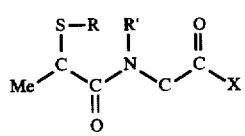

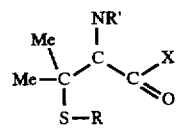

The radical X can be chosen from the group consisting of —O—R' and —NRR'. The radicals R, R' and R" independently of one another are: H, $C_{1-18}$-alkyl or -alkenyl or $C_{1-18}$-acyl.

It is preferable here to choose the organic radicals such that the organic radicals R, R' and R" independently of one another are: H, ethyl or acetyl. X can advantageously symbolize the —NH₂ group.

The salts or acid or base adducts of the thiols or thiol derivatives according to the invention furthermore are of advantage.

Examples of thiols and thiol derivatives which are particularly preferred according to the invention are

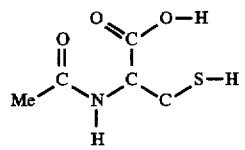

(N-Acetylcysteine)

Compound I

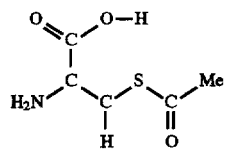

(S-Acetylcysteine)

Compound II

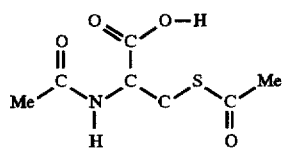

(N,S-Diacetylcysteine)

Compound III

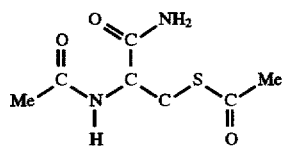

(N,S-Diacetylcysteinamide)

Compound IV

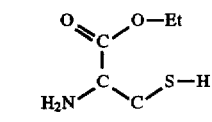

(Cysteine ethyl ester)

Compound V

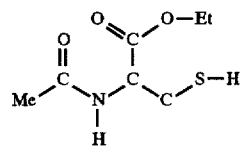

(N-Acetylcysteine ethyl ester)

Compound VI

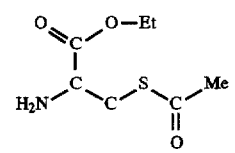

(S-Acetylcysteine ethyl ester)

Compound VII

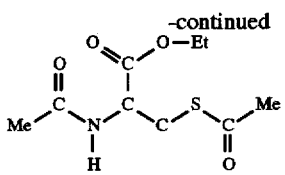

(N,S-Diacetylcysteine ethyl ester)

Compound VIII

The salts or acid or base adducts of these particularly preferred thiols and thiol derivatives are also preferred.

The invention accordingly also relates to the use of thiols or thiol derivatives for protecting the skin against the harmful influence of ultraviolet light.

It has been found, astonishingly, that the thiols or thiol derivatives according to the invention are capable of trapping photochemically produced free radicals, of protecting against photochemically induced, uncontrolled oxidation processes, and even of "quenching" singlet oxygen, that is to say converting it into the triplet ground state by a physicochemical process. Substances having this property are also called "quenching agents".

The invention therefore also relates to the use of thiols or thiol derivatives as an agent which traps free radicals, antioxidant and/or quenching agent for photochemically produced reactive substances, such as singlet oxygen.

The cosmetic and/or dermatological formulations according to the invention can have the customary composition and can be used for treatment of the skin and/or hair in the context of dermatological treatment or treatment in the context of care cosmetics. However, they can also be used in make-up products in decorative cosmetics. They preferably comprise 0.01% by weight to 10% by weight, but in particular 0.1% by weight to 6% by weight, based on the total weight, of one or more thiols or thiol derivatives.

For use, the thiols or thiol derivatives according to the invention are applied to the skin and/or hair in an adequate amount in the manner customary for cosmetics and dermatological agents.

Those cosmetic and dermatological formulations which are in the form of a sunscreen agent are particularly preferred. These preferably additionally comprise at least one UVA filter and/or at least one UVB filter and/or at least one inorganic pigment.

Cosmetic formulations according to the invention for protecting the skin from UV rays can be in various forms, such as are usually employed, for example, for this type of formulation. They can thus be, for example, a solution, an emulsion of the water-in-oil (W/O) type or of the oil-in-water (O/W) type, or a multiple emulsion, for example of the water-in-oil-in-water (W/O/W) type, a gel, a hydrodispersion, a solid stick or also an aerosol.

The cosmetic formulations according to the invention can comprise cosmetic auxiliaries such as are usually used in such formulations, for example preservatives, bactericides, perfumes, agents for preventing foaming, dyestuffs, pigments which have a colouring action, thickening agents, surface-active substances, emulsifiers, softening, moistening and/or humectant substances, fats, oils, waxes or other customary constituents of a cosmetic formulation, such as alcohols, polyols, polymers, foam stabilisers, electrolytes, organic solvents or silicon derivatives.

If the cosmetic or dermatological formulation is a solution or lotion, solvents which can be used are:
water or aqueous solutions;
oils, such as triglycerides of capric or of caprylic acid, but preferably castor oil;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. In the case of alcoholic solvents, water can be a further constituent.

Emulsions according to the invention, for example in the form of a sunscreen cream, a sunscreen lotion or a sunscreen milk, are advantageous and comprise, for example, the fats, oils, waxes and other fatty substances mentioned, as well as water and an emulsifier, such as is usually used for such a type of formulation.

Gels according to the invention usually comprise alcohols of low C number, for example ethanol, isopropanol, 1,2-propanediol or glycerol, and water or an abovementioned oil in the presence of a thickening agent, which is preferably silicon dioxide or an aluminium silicate in oily-alcoholic gels and preferably a polyacrylate in aqueous-alcoholic or alcoholic gels.

Solid sticks according to the invention comprise, for example, naturally occurring or synthetic waxes, fatty alcohols or fatty acid esters. Lip-care sticks are preferred.

Suitable propellants for cosmetic or dermatological formulations according to the invention which can be sprayed from aerosol containers are the customary known readily volatile, liquefied propellants, for example hydrocarbons (propane, butane or isobutane), which can be employed by themselves or as a mixture with one another. Compressed air can also advantageously be used.

The expert of course knows that there are nontoxic propellant gases per se which would be suitable in principle for the present invention, but which nevertheless should be dispensed with because of their unacceptable action on the environment or other concomitant circumstances, in particular fluorohydrocarbons and fluorochlorohydrocarbons (FCHCs).

The cosmetic and dermatological formulations for protection of the skin comprise the thiols or thiol derivatives according to the invention, for example, in amounts of 0.01–10% by weight, preferably in amounts of 0.1–6% by weight, but in particular 0.5–5% by weight, based on the total weight of the formulation.

The formulations according to the invention can preferably furthermore comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulation, in order to provide cosmetic formulations which protect the skin from the entire range of ultraviolet radiation. They can also be used as sunscreen agents.

The UVB filters can be oil-soluble or water-soluble. Oil-soluble substances which may be mentioned are, for example:

3-benzylidenecamphor derivatives, preferably 3-(4-methylbenzylidene)camphor and 3-benzylidenecamphor;

4-aminobenzoic acid derivatives, preferably 2-ethyl-hexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4-methylbenzophenone and 2,2'-dihydroxy-4-methoxybenzophenone;

esters of benzalmalonic acid, preferably di-2-ethyl-hexyl 4-methoxybenzalmalonate; and 2,4,6-trianilino-(p-carbo-2'-ethyl-1'-hexyloxy)-1,3,5-triazine.

Water-soluble substances which may be mentioned are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)sulphonic acid and their salts.

The list of UVB filters mentioned, which can be used in combination with the thiols or thiol derivatives according to the invention, is of course not intended to be limiting.

The invention also relates to the combination of one or more thiols or thiol derivatives according to the invention with one or more UVB filters and to cosmetic or dermatological formulations according to the invention which also comprise one or more UVB filters.

It may also be advantageous to combine one or more thiols or thiol derivatives according to the invention with UVA filters which were hitherto usually contained in cosmetic and/or dermatological formulations. These substances are preferably derivatives of dibenzoylmethane, in particular 1-(4'-tert-butylphenyl)-3-(4'-methoxphenyl)propane-1,3-dione and 1-phenyl-3-(4'-isopropylphenyl)propane-1,3-dione. The invention also relates to these combinations and to formulations comprising these combinations. The amounts used for the UVB combination can be employed.

Advantageous formulations furthermore are obtained if the thiols or thiol derivatives according to the invention are combined with UVA filters and UVB filters.

Cosmetic formulations comprising thiols can also comprise inorganic pigments which are usually used in cosmetics for protection of the skin from UV rays. These are oxides of titanium, zinc, iron, zirconium, silicon, manganese, aluminium and cerium and mixtures thereof, as well as modifications in which the oxides are the active agents. They are particularly preferably pigments based on titanium dioxide.

The invention also relates to these combinations of UVA filter and/or UVB filter and pigment and to formulations comprising this combination. The amounts mentioned for the above combinations can be used.

Cosmetic formulations according to the invention for protection of the hair from UV rays are, for example, shampooing agents, formulations which are used when rinsing the hair before or after shampooing, before or after permanent wave treatment or before or after colouring or bleaching of the hair, formulations for blow-drying or setting hair, formulations for colouring or bleaching, a styling and treatment lotion, a hair spray or permanent wave agents. The cosmetic formulations comprise active compounds and auxiliaries such as are usually used for this type of formulation for hair care and hair treatment. Auxiliaries which can be used are preservatives, surface-active substances, substances for preventing foaming, emulsifiers, thickening agents, fats, oils, waxes, organic solvents, bactericides, perfumes, dyestuffs or pigments, the task of which is to colour the hair or the formulation itself, electrolytes and formulations against the hair becoming greasy.

Cosmetic formulations which are a shampooing agent preferably comprise at least one anionic, non-ionic or amphoteric surface-active substance, or mixtures of such substances, at least one thiol or thiol derivative according to the invention in an aqueous medium, and auxiliaries such as are usually used for this purpose. The surface-active substance can be present in the shampooing agent in a concentration of between 1% by weight and 50% by weight.

If the cosmetic or dermatological formulation is in the form of a lotion which is rinsed out and is used, for example, before or after bleaching, before or after shampooing, between two shampooing steps or before or after permanent wave treatment, it comprises, for example, aqueous or aqueous-alcoholic solutions, which optionally comprise surface-active substances, preferably non-ionic or cationic surface-active substances, the concentration of which can be between 0.1 and 10% by weight, preferably between 0.2 and 5% by weight. This cosmetic or dermatological formulation can also be an aerosol comprising the auxiliaries usually used for this purpose.

A cosmetic formulation in the form of a lotion which is not rinsed out, in particular a lotion for setting hair, a lotion used when blow-drying the hair or a styling and treatment lotion, is in general an aqueous, alcoholic or aqueous-alcoholic solution and comprises at least one cationic, anionic, non-ionic or amphoteric polymer or also mixtures thereof, as well as at least one thiol or thiol derivative according to the invention. The amount of polymers used is, for example, between 0.1 and 10% by weight, preferably between 0.1 and 3% by weight.

Cosmetic and dermatological formulations for treatment and care of hair which comprise at least one thiol or thiol derivative according to the invention can be in the form of emulsions which are of the non-ionic or anionic type. Non-ionic emulsions comprise, in addition to water, oils or fatty alcohols, which, for example, can also be polyethoxylated or polypropoxylated, or also mixtures of the two organic components. These emulsions optionally comprise cationic surface-active substances. Anionic emulsions are preferably of the type of a soap and comprise at least one thiol or thiol derivative according to the invention having an anionic or non-ionic character.

Cosmetic and dermatological formulations for treatment and care of hair can be in the form of gels which, in addition to at least one thiol or thiol derivative according to the invention and solvents usually used for this purpose, also comprise organic thickening agents, for example gum arabic, xanthan gum, sodium alginate or cellulose derivatives, preferably methylcellulose, hydroxymethylcellulose, hydroxyethylcellulose, hydroxypropylcellulose or hydroxypropylmethylcellulose, or inorganic thickening agents, for example aluminium silicates, such as, for example, bentonites, or a mixture of polyethylene glycol and polyethylene glycol stearate or distearate. The gel comprises the thickening agent, for example, in an amount of between 0.1 and 30% by weight, preferably between 0.5 and 15% by weight.

The amount of the thiols or thiol derivatives according to the invention in an agent intended for hair is preferably 0.01% by weight to 10% by weight, in particular 0.5% by weight to 5% by weight, based on the total weight of the formulations.

The present invention also relates to a method for protecting the skin and hair from UVA and UVB radiation, which is characterized in that an adequate amount of a cosmetic or dermatological formulation which comprises at least one thiol or thiol derivative according to the invention is applied to the skin or hair, and to the use of these compounds in particular for these purposes.

The present invention also relates to a method for protecting colourless or coloured cosmetic and dermatological formulations against UVA and UVB rays, and to these formulations, which are, for example, abovementioned formulations for treatment and care of the hair, in particular hair colouring agents, hair sprays, shampooing agents or colour shampooing agents, make-up products, such as, for example, nail varnishes, lipsticks, complexion foundations and creams for treatment of the skin, or all other cosmetic formulations, the constituents of which may cause stability problems because of light during storage, characterized in that at least one thiol or thiol derivative according to the invention is added to the cosmetic or dermatological formulations in an amount adequate for stabilization against light, in particular UVA rays.

The amount of compounds according to the invention in these formulations is preferably 0.01% by weight to 10% by weight, in particular 0.1% by weight to 3% by weight, based on the total weight of the formulations.

All the amounts data, contents and percentages are based on the weight and the total amount or on the total weight of the formulations, unless stated otherwise.

The invention also relates to the process for the preparation of the cosmetic formulations according to the invention, which is characterized in that thiols or thiol derivatives according to the invention are incorporated into cosmetic or dermatological formulations in a manner which is known per se.

The following examples are intended to illustrate the present invention without limiting it.

|  | % by weight |
|---|---|
| Example 1 | |
| Cyclomethicone | 2.000 |
| Cetyldimethicone copolyol | 0.200 |
| PEG-22-dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Compound II | 0.500 |
| ZnSO$_4$ | 0.700 |
| Na$_4$EDTA | 0.300 |
| Perfume, preservative, dyestuffs | as required |
| H$_2$O, completely demineralized | to 100.000 |
| Example 2 | |
| Cyclomethicone | 2.000 |
| Cetyldimethicone copolyol | 0.200 |
| PEG-22-dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethene | 4.000 |
| Compound II | 0.500 |
| ZnSO$_4$ | 0.700 |
| Na$_4$EDTA | 0.300 |
| Perfume, preservative, dyestuffs | as required |
| H$_2$O, completely demineralized | to 100.000 |
| Example 3 | |
| Cyclomethicone | 2.000 |

|  | % by weight |
|---|---|
| Cetyldimethicone copolyol | 0.200 |
| PEG-22-dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Compound III | 2.500 |
| ZnSO$_4$ | 0.700 |
| Na$_4$EDTA | 0.300 |
| Perfume, preservative, dyestuffs | as required |
| H$_2$O, completely demineralized | to 100.000 |

Example 4

|  | % by weight |
|---|---|
| Cyclomethicone | 2.000 |
| Cetyldimethicone copolyol | 0.200 |
| PEG-22-dodecyl copolymer | 3.000 |
| Paraffin oil (DAB 9) | 2.000 |
| Caprylic acid/capric acid triglyceride | 5.800 |
| Octyl methoxycinnamate | 5.800 |
| Butyl-methoxy-dibenzoylmethane | 4.000 |
| Compound IV | 3.000 |
| ZnSO$_4$ | 0.700 |
| Na$_4$EDTA | 0.300 |
| Perfume, preservative, dyestuffs | as required |
| H$_2$O, completely demineralized | to 100.000 |

Example 5

|  | % by weight |
|---|---|
| Cyclomethicone | 2.000 |
| Cetearyl alcohol + PEG-40-hydrogenated castor oil + sodium cetearyl-sulphate | 2.500 |
| Glyceryl lanolate | 1.000 |
| Caprylic acid/capric acid triglyceride | 0.100 |
| Laurylmethicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 0.500 |
| Compound V | 1.750 |
| Na$_3$HEDTA | 1.500 |
| Perfume, preservative, dyestuffs | as required |
| H$_2$O, completely demineralized | to 100.000 |

Example 6

|  | % by weight |
|---|---|
| Cyclomethicone | 2.000 |
| Cetearyl alcohol + PEG-40-hydrogenated castor oil + sodium cetearyl-sulphate | 2.500 |
| Glyceryl lanolate | 1.000 |
| Caprylic acid/capric acid triglyceride | 0.100 |
| Laurylmethicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 0.750 |
| Compound VI | 2.500 |
| Na$_3$HEDTA | 1.500 |
| Perfume, preservative, dyestuffs | as required |
| H$_2$O, completely demineralized | to 100.000 |

Example 7

|  | % by weight |
|---|---|
| Cyclomethicone | 2.000 |
| Cetearyl alcohol + PEG-40-hydrogenated castor oil + sodium cetearyl-sulphate | 2.500 |
| Glyceryl lanolate | 1.000 |
| Caprylic acid/capric acid triglyceride | 0.100 |
| Laurylmethicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 1.000 |
| Compound VII | 0.700 |
| Na$_3$HEDTA | 1.500 |
| Perfume, preservative, dyestuffs | as required |
| H$_2$O, completely demineralized | to 100.000 |

Example 8

|  | % by weight |
|---|---|
| Cyclomethicone | 2.000 |
| Cetearyl alcohol + PEG-40-hydrogenated castor oil + sodium cetearyl-sulphate | 2.500 |
| Glyceryl lanolate | 1.000 |
| Caprylic acid/capric acid triglyceride | 0.100 |
| Laurylmethicone copolyol | 2.000 |
| Octyl stearate | 3.000 |
| Castor oil | 4.000 |
| Glycerol | 3.000 |
| Acrylamide/sodium acrylate copolymer | 0.300 |
| Hydroxypropylmethylcellulose | 0.300 |
| Octyl methoxycinnamate | 5.000 |
| Butyl-methoxy-dibenzoylmethane | 0.500 |
| Compound VIII | 1.600 |
| Na$_3$HEDTA | 1.500 |
| Perfume, preservative, dyestuffs | as required |
| H$_2$O, completely demineralized | to 100.000 |

We claim:

1. Cosmetic or dermatological sunscreen formulations, comprising thiols and/or thiol derivatives selected from the group consisting of S-acetylcysteine, S-acetylcysteine alkyl esters, S, N-diacetylcysteine, S, N-diacetylcysteine alkyl esters and their cosmetically or pharmaceutically acceptable salts or acid or base adducts wherein the alkyl radicals of the thiols or thiol derivatives which are present as alkyl esters being alkyl radicals having 1 to 18 carbon atoms in combination with amounts of substances effective for protecting the skin from UV light selected from the group consisting of 1-(4'-tert-butylphenyl)-3-(4'-methoxyphenyl)propane-1,3-dione, 1-phenyl-3-(4'-isopropylphenyl)propane-1,3-dione and mixtures thereof.

2. Formulations according to claim 1, wherein the thiols or thiol derivatives are present as alkyl esters.

3. Formulations according to claim 2, wherein the alkyl radicals of the thiols or thiol derivatives which are present as alkyl esters are ethyl radicals.

4. Formulations according to claim 1, wherein the light protection formulations have a content of 0.01–10% by weight of the thiols or thiol derivatives based on the total weight of formulation.

5. Cosmetic or dermatological sunscreen formulations, comprising thiols and/or thiol derivatives selected from the group consisting of S-acetylcysteine, S-acetylcysteine alkyl esters, S,N-diacetylcysteine, S,N-diacetylcysteine alkyl esters and their cosmetically or pharmaceutically acceptable salts or acid or base adducts wherein the alkyl radicals of the thiols or thiol derivatives which are present as alkyl esters being alkyl radicals having 1 to 18 carbon atoms in combination with amounts of substances effective for protecting the skin from UV light selected from the group consisting of 1-(4'-tert-butylphenyl)-3-(4'-methoxyphenyl)propane-1,3-dione, 1-phenyl-3-(4'-isopropylphenyl)propane-1,3-dione, butyl-methoxy-dibenzoylmethane and mixtures thereof.

6. Formulations according to claim 5, wherein the thiols or thiol derivatives are present as alkyl esters.

7. Formulations according to claim 5, wherein the alkyl radicals of the thiols or thiol derivatives which are present as alkyl esters are ethyl radicals.

8. Formulations according to claim 5, wherein the light protection formulations have a content of 0.01–10% by weight of the thiols or thiol derivatives based on the total weight of formulation.

* * * * *